United States Patent
Fleddermann et al.

(10) Patent No.: US 11,898,962 B2
(45) Date of Patent: Feb. 13, 2024

(54) METHOD AND SYSTEM FOR DETERMINING THE LOCATION OF ARTEFACTS AND/OR INCLUSIONS IN A GEMSTONE, MINERAL, OR SAMPLE THEREOF

(71) Applicant: The Australian National University, Acton (AU)

(72) Inventors: Roland Fleddermann, Bruce (AU); Jong Hann Chow, Bonner (AU); Adrian Paul Sheppard, Fisher (AU); Timothy John Senden, Acton (AU); Shane Jamie Latham, Griffith (AU); Keshu Huang, Turner (AU)

(73) Assignee: The Australian National University, Acton (AU)

( * ) Notice: Subject to any disclaimer, the term of this patent is extended or adjusted under 35 U.S.C. 154(b) by 631 days.

(21) Appl. No.: 16/977,622

(22) PCT Filed: Mar. 4, 2019

(86) PCT No.: PCT/AU2019/050182
§ 371 (c)(1),
(2) Date: Sep. 2, 2020

(87) PCT Pub. No.: WO2019/165514
PCT Pub. Date: Sep. 6, 2019

(65) Prior Publication Data
US 2021/0041369 A1      Feb. 11, 2021

(30) Foreign Application Priority Data
Mar. 2, 2018  (AU) ................................ 2018900677

(51) Int. Cl.
*G01N 21/00*     (2006.01)
*G01N 21/87*     (2006.01)
(Continued)

(52) U.S. Cl.
CPC ......... *G01N 21/87* (2013.01); *G01B 9/02091* (2013.01); *G01B 11/005* (2013.01);
(Continued)

(58) Field of Classification Search
CPC .... G01N 21/87; G01N 21/88; G01N 21/8851; G01N 2021/8477; G01N 2021/8861;
(Continued)

(56) References Cited

U.S. PATENT DOCUMENTS

| 5,901,198 A | 5/1999 | Crawford et al. |
| 7,042,556 B1 | 5/2006 | Sun |

(Continued)

FOREIGN PATENT DOCUMENTS

| EP | 1211503 A1 | 5/2002 | |
| WO | WO-03099054 A2 * | 12/2003 | ............. G01N 21/87 |

(Continued)

OTHER PUBLICATIONS

Preliminary International Report on Patentability dated Jun. 16, 2018 in related International Application No. PCT/AU2019/050182.

(Continued)

*Primary Examiner* — Uzma Alam
*Assistant Examiner* — Jonathon Cook
(74) *Attorney, Agent, or Firm* — Dinsmore & Shohl LLP (57) ABSTRACT

A method and system for determining a location of artefacts and/or inclusions in a gemstone, mineral or sample thereof, the method comprising the steps of: surface mapping a gemstone, mineral or sample thereof to determine surface geometry associated with at least a portion of a surface of the gemstone, mineral or sample thereof; sub-surface mapping the gemstone, mineral or sample thereof using an optical beam that is directed at the surface along an optical beam path, wherein the optical beam is generated by an optical (Continued)

source using an optical tomography process; determining a surface normal at the surface at an intersection point between the optical beam path and the determined surface geometry; determining relative positioning between the surface normal and the optical beam path; and determining the location of artefacts and/or inclusions in the gemstone, mineral or sample thereof based on the sub-surface mapping step and the determined relative positioning.

18 Claims, 8 Drawing Sheets

(51) Int. Cl.
| | | |
|---|---|---|
| *G06T 7/73* | (2017.01) | |
| *G06T 7/521* | (2017.01) | |
| *G01B 9/02091* | (2022.01) | |
| *G01B 11/00* | (2006.01) | |
| *G01B 11/30* | (2006.01) | |
| *G01N 21/88* | (2006.01) | |
| *G01N 23/046* | (2018.01) | |
| *G01N 23/083* | (2018.01) | |
| *G01N 33/38* | (2006.01) | |

(52) U.S. Cl.
CPC ......... *G01B 11/30* (2013.01); *G01N 21/8851* (2013.01); *G01N 23/046* (2013.01); *G01N 23/083* (2013.01); *G01N 33/381* (2013.01); *G06T 7/521* (2017.01); *G06T 7/74* (2017.01); *G01N 2021/8861* (2013.01); *G01N 2223/04* (2013.01); *G01N 2223/3304* (2013.01); *G01N 2223/419* (2013.01); *G01N 2223/646* (2013.01); *G06T 2207/10028* (2013.01); *G06T 2207/10081* (2013.01); *G06T 2207/10101* (2013.01)

(58) Field of Classification Search
CPC .............. G01N 23/046; G01N 23/83; G01N 2223/419; G01N 2223/646; G01N 33/381; G06T 7/74; G06T 7/521; G06T 2207/10101; G01B 9/02091; G01B 9/0209; G01B 11/005
See application file for complete search history.

(56) References Cited

U.S. PATENT DOCUMENTS

| | | |
|---|---|---|
| 2006/0062446 A1 | 3/2006 | Porat |
| 2008/0231833 A1 | 9/2008 | Shlezinger et al. |
| 2012/0027475 A1 | 11/2012 | Smith et al. |
| 2014/0107986 A1 | 4/2014 | Sivovolenko et al. |
| 2016/0013905 A1 | 5/2016 | Patel |
| 2016/0139058 A1 | 5/2016 | Patel |
| 2018/0372647 A1* | 12/2018 | Brenner ............ G01N 21/8806 |

FOREIGN PATENT DOCUMENTS

| | | |
|---|---|---|
| WO | 2008102361 A2 | 8/2008 |
| WO | 2009068354 A1 | 6/2009 |
| WO | 2011054822 A1 | 5/2011 |
| WO | 2017112609 A1 | 6/2017 |

OTHER PUBLICATIONS

International Search Report dated Mar. 29, 2019 in related International Application No. PCT/AU2019/050182.

* cited by examiner

METHOD AND SYSTEM FOR DETERMINING THE LOCATION OF ARTEFACTS AND/OR INCLUSIONS IN A GEMSTONE, MINERAL, OR SAMPLE THEREOF

TECHNICAL FIELD

The present invention relates generally to a method and system for determining the location of artefacts and/or inclusions in a gemstone, mineral or sample thereof.

BACKGROUND

Gemstones (such as diamonds, rubies etc.), minerals, or samples thereof are generally analysed to detect unwanted artefacts and/or inclusions in order to enable them to be optimally cut to enable the best value yield. For example, to be more efficiently cut while avoiding the artefacts and/or inclusions. Techniques for diamond inclusion mapping have been evaluated, including X-ray micro-computed tomography (XCT), optical coherence tomography (OCT) or optical projection tomography (OPT), as described in the following.

In the case of XCT, imaging and 3-dimensional reconstruction has been performed by calculating the attenuation distribution across the object from multi-angular projected images. Due to the capability of X-rays to penetrate solid materials to varying degrees without refraction, XCT can perform a geometrically accurate and non-invasive analysis for diamond internal morphology. However, X-ray attenuation measurements do not provide good contrast for all types of artefacts, and it is generally accepted that XCT is unable to identify all inclusion types and to sufficiently resolve cracks at a feasible cost and time.

Another technique used is optical projection tomography (OPT). For OPT, the imaging principle is similar to XCT, but light is used in the optical wavelength range (roughly 400-800 nm) instead of X-ray to produce the projection image. Like most other projection tomography techniques, OPT is reported to have high resolvability, benefitting from the (relatively) short operating wavelength. Since optical wavelengths are used for imaging, this technique is able to detect most inclusion types, including graphite at a reduced system cost compared to an XCT system. However, operating at optical wavelengths has the detrimental effect of introducing complexity in the interaction between the sample and optical light. In standard OPT applications for (rough) diamond imaging, samples need to be submerged in refractive index matching materials to reduce the scattering and make light paths entering the sample approximately straight lines, such that the 3-dimensional distribution of light absorption across the sample can be calculated using standard back projection algorithms. For diamond imaging, due to the high refractive index of diamond, the matching material is often liquid selenium, a toxic material for which special handling is required. Furthermore, these materials may contaminate the sample. These complexities limit the utility of techniques that require index matching to achieve accurate mapping of internals.

In contrast, optical coherence tomography (OCT) performs 3D imaging by measuring the reflective and back-scattering profile across the sample using low coherence interferometry. This technique can achieve images with about 10 μm resolution and high sensitivity. Though some work has been reported in mineralogy studies for using OCT to inspect jade and glass, in these applications OCT is usually restricted to the surface morphology. The main difference with OCT compared to many other 3-dimensional imaging techniques is that OCT uses confocal reflectometry instead of solving an inverse problem, and that it operates in the near infrared wavelength range (typically 800 to 1500 nm), which makes it sensitive to carbon inclusions. When appropriate refractive index and surface refraction corrections (as described herein) are applied, OCT can further be performed without the need for an index matching material.

In summary, although these techniques (XCT, OCT and OPT) may have some advantageous features, neither of them alone are ideally suited to detect and accurately map artefacts in gemstones due to the aforementioned disadvantages of limited detectability or practical issues of requiring special procedures and or treatment of the samples.

On the other hand, studies of integrated techniques (e.g. X-ray and fluorescence) produce fused images which show great potential to improve the imaging result beyond the limitation of a single technique. This type of multi-modal imaging can be achieved both in real-time through hardware or fusing images from a separate system via post processing. While the post processing method at first glance seems more flexible and affordable, actual implementations of such an algorithm typically involve iterative approaches for the estimation of alignment parameters and therefore require large amounts of computing power. Furthermore, such algorithms are not always stable and, depending on the input data situations, reliable results may not be found.

SUMMARY

It is an object of the present invention to substantially overcome, or at least ameliorate, one or more disadvantages of existing arrangements.

Disclosed are arrangements which seek to address the above problems by providing an improved method and system for detecting the location of artefacts in a gemstone, mineral, or sample thereof.

According to a first aspect of the present disclosure, there is provided a method for determining a location of artefacts and/or inclusions in a gemstone, mineral or sample thereof, the method comprising the steps of: surface mapping a gemstone, mineral or sample thereof to determine surface geometry associated with at least a portion of a surface of the gemstone, mineral or sample thereof; sub-surface mapping the gemstone, mineral or sample thereof using an optical beam that is directed at the surface along an optical beam path, wherein the optical beam is generated by an optical source using an optical tomography process; determining a surface normal at the surface at an intersection point between the optical beam path and the determined surface geometry; determining relative positioning between the surface normal and the optical beam path; and determining the location of artefacts and/or inclusions in the gemstone, mineral or sample thereof based on the sub-surface mapping step and the determined relative positioning.

According to a second aspect of the present disclosure, there is provided system for determining a location of artefacts and/or inclusions in a gemstone, mineral or sample thereof, the system comprising: a surface mapping device arranged to surface map a gemstone, mineral or sample thereof to determine surface geometry associated with at least a portion of a surface of the gemstone, mineral or sample thereof; a sub-surface mapping device arranged to sub-surface map the gemstone, mineral or sample thereof using an optical beam that is directed at the surface along an optical beam path, wherein the optical beam is generated by an optical source using an optical tomography process; a computing system arranged to determine a surface normal at the surface at an intersection point between the optical beam path and the determined surface geometry; determine relative positioning between the surface normal and the optical beam path; and determine the location of artefacts and/or inclusions in the gemstone, mineral or sample thereof based on the sub-surface mapping step and the determined relative positioning.

Other aspects are also disclosed.

BRIEF DESCRIPTION OF THE DRAWINGS

At least one embodiment of the present invention will now be described with reference to the drawings and appendices, in which.

DETAILED DESCRIPTION INCLUDING BEST MODE

Where reference is made in any one or more of the accompanying drawings to steps and/or features, which have the same reference numerals, those steps and/or features have for the purposes of this description the same function(s) or operation(s), unless the contrary intention appears.

It will be understood that references to the herein described methods and systems in relation to artefacts also apply to the same methods or systems in relation to inclusions, and vice versa.

In the context of this application, "artefacts" is intended to mean a naturally or manmade irregularity and includes but is not exclusive to: voids, cracks, mineral inclusions, natural formations, growth patterns etc. Embodiments of the invention aim to detect all such artefacts that are visible to the naked eye as well as under levels of magnification such as 10× which is the typical magnification for detection of imperfections for grading of diamonds, but may include artefacts visible at other levels of magnifications and other gemstones, minerals, or samples thereof.

The herein described example is with reference to a gemstone, such as a diamond or the like. It will be understood however that the herein described method, process or system can be applied to any transparent or semi-transparent gemstone, mineral or sample thereof. For example, a semi-transparent gemstone, mineral or sample thereof may have a frosted coating. The term "sample" may refer to a whole or a portion of a gemstone or a mineral, and may refer to a pre-cut or post-cut gemstone or mineral.

A brief description of an optical tomography process using OCT is now provided.

OCT is based on low-coherence or white light interferometry. For illustrative purpose, only one implementation of the technique, called time-domain optical coherence tomography (TD-OCT), is discussed. It will be understood that other variations may also be used where they use the same underlying principle but with a different implementation. For example, frequency domain optical coherence tomography (FD-OCT), which is further split into spectral domain and swept source OCT, may be used.

Light in a time domain OCT system is broken into two arms—a sample arm and a reference arm using a beam splitter. The reference arm contains a movable mirror which reflects light back towards the beam splitter with a variable, time dependent arm-length. The object of interest is placed into the sample arm. Light scattered from inside the sample also travels back towards the beam splitter and interferes with the light from the reference arm.

Owing to the short coherence length of the light source, an interference pattern is only observed when the arm length of the reference and the sample arm are matched to within the coherence length of the source, typically in the order of micrometers. By recording the interference pattern while the length of the reference arm is varied, one can retrieve depth resolved back-scatter amplitude information from the sample. This data can be used to reconstruct a full volumetric map of the sample by laterally scanning the beam across the sample surface in two dimensions, using e.g. a galvanometric mirror scanner. Combining the depth information from all individual scans one can reconstruct cross-sectional images (scanning in one lateral dimension) and full volumes (combining multiple cross-sectional images obtained at different positions in the other lateral dimension).

According to various embodiments described in more detail below, a surface mapping device is arranged to map a gemstone to determine the surface geometry associated with at least a portion of a surface of the gemstone. For example, the surface geometry of the entire gemstone surface may be obtained by an XCT machine or an OCT machine. As a further example, the surface geometry of a portion of the gemstone surface may be obtained.

As part of an optical tomography process, a sub-surface mapping device is arranged to scan the gemstone using an optical beam that is directed at the surface of the gemstone in order to detect co-ordinate locations of artefacts. It will be understood that the artefacts may be visible to the naked eye, or may not be visible to the naked eye, whether under a microscope or not. The artefact should at least however be visible to, or detectable by, the equipment (e.g. optical sensing equipment) being used to detect the artefact.

According to one example, the process used is an optical tomography process where a sub-surface mapping device is arranged to scan the gemstone using an optical beam that is directed at the surface of the gemstone in order to detect co-ordinate locations of visual artefacts. The term "visual" is intended to mean visual in terms of the frequency of the optical beam being used to scan the gemstone. A variety of optical frequencies could be used in the embodiments described herein. Several optical techniques for sub-surface scanning exist, and these can employ a wide range of optical frequencies, ranging from visible to infrared. In embodiments of the invention, light in the visible range may be used to ensure detection of artefacts visible to the human eye. However, it will be understood that artefacts that affect the passage of visible light in such a way that they are able to be detected by a sub-surface scanning technique (e.g. scattering in the case of OCT or absorption in the case of OPT) are likely to similarly affect near-infrared wavelengths which are more commonly employed in optical coherence tomography systems and that such wavelengths can thus also be used as a proxy for the detection of artefacts visible to the human eye. The optical beam is directed along an optical beam path outside of the gemstone from the optical source to the gemstone surface. The co-ordinate locations may be used to generate a full map of the locations of the visual artefacts (or inclusions) in the gemstone. For example, an OCT or OPT machine may be used to map the sub-surface of the gemstone.

The surface mapping and sub-surface mapping in this example are non-destructive processes in that the gemstone being scanned is not destroyed during the mapping step(s), physical interference such as markings, polishing sections of the sample to form a window, surface treatment or refractive index matching are not required.

The gemstone may be located on a platform or may be clamped in a suitable device, or held in a suitable position using any other suitable means for holding the gemstone.

A computing device (explained in detail below) is connected to the different devices and pieces of equipment to control their operation and capture the data that is generated. The computing equipment uses the data captured by the first device during the surface mapping stage to generate the surface geometry. For example, multiple two dimensional images (e.g. radiographs) of the gemstone at different positions may be captured by the XCT machine. These two dimensional images may be combined together to generate a three dimensional surface geometry.

In one example, the surface geometry may be used by the computing device to determine a surface normal at the surface of the gemstone at each point that intersects (intersection point) with the optical beam path of the beam generated during the sub-surface mapping stage. That is, for each point on the gemstone, where the beam impacts the surface of the gemstone, a surface normal is calculated.

It will be understood that, as an alternative to determining the surface normal a determination may be made of the relative orientation of the surface geometry at the surface at an intersection point between the optical beam path and the determined surface geometry. That is, the system is not required specifically to use the surface normal, but may use any other suitable relative orientation measurement and adjust the calculations as needed.

The computing device may use the calculated surface normal (or other relative orientation) and the known optical beam path to determine the relative positioning between the surface normal and the known optical beam path. That is, an angle of incidence is determined that provides a value of the deviation of the optical beam path from the surface normal (or other relative orientation). Where the surface is a rough surface, an average angle of incidence may be determined over the surface area being mapped, or if the surface mapping captures some characteristics of the roughness, a multiplicity of surface normals may be determined, leading to a multiplicity of angles of incidence.

The computing device then generates three dimensional co-ordinates of visual artefacts, which may then be used to generate a three dimensional map of the location of the visual artefacts within the gemstone based on the co-ordinate data obtained during the sub-surface mapping step and the determined relative positioning between the surface normal (or other relative orientation) and the known optical beam path. The generation of the three dimensional co-ordinates (and the subsequent map) may be performed using many different techniques as described in detail below.

Figure 1A:
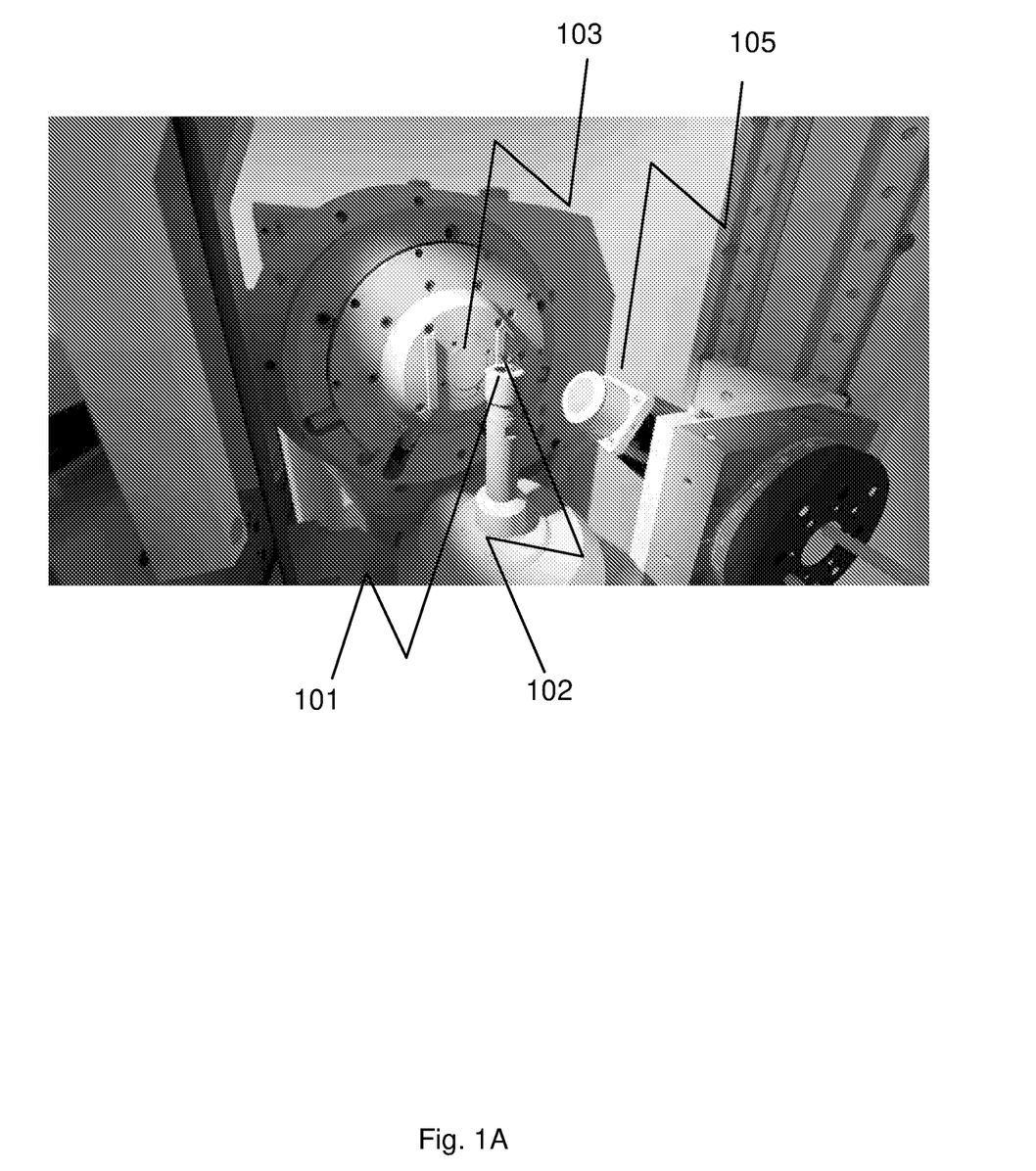
FIG. 1A shows an image of a system arranged to determine the location of artefacts in a gemstone according to the present disclosure.

FIG. 1A shows an image of a system arranged to carry out the process of detecting visual artefacts in a gemstone.

According to this example, the system has a platform 101 upon which a gemstone 102 can be placed. The platform in this example rotates. An X-ray computed tomography (XCT) machine (surface mapping device) 103 is positioned to take an X-ray image of the gemstone in order to map the gemstone and determine the surface geometry of the gemstone. An optical coherence tomography (OCT) machine (sub-surface mapping device) 105 is positioned to map the sub-surface of the gemstone.

During the surface mapping by the surface mapping device, multiple two dimensional images are created using X-rays, and these multiple images are used to create a three dimensional map of the surface geometry of the gemstone.

The OCT machine 105 is arranged to move up and down in a vertical direction (z-axis). It is also arranged to rotate on (or about) the z-axis. The platform is arranged to rotate relative to the OCT machine. In this example, by placing the gemstone on the platform, the relative position of the gemstone on the platform with respect to the optical beam generated by the OCT machine can be adjusted.

The platform and surface mapping device are set up and controlled to produce a helical scanning movement, where the relative position of the gemstone and the x-ray beam path is scanned helically. That is, the platform is rotated on the z-axes at the same time as it is moved up or down on the z-axis to produce the helical relative movement.

It will be understood that alternative scanning movements that are non-helical may be used as appropriate as will be understood by a person skilled in the art. For example, examples of non-helical trajectories are (a) circular (b) multi-circle, (c) multi-turn helix, (d) double helix, (e) an irregular trajectory, such as a non-lattice-like distribution of points on the 2D space of source locations at a single distance. It will also be understood that images may be captured using continuous scanning as well as stop-start scanning.

To calculate the surface geometry of the gemstone the following process may be applied.

Hardware is defined through a coordinate system (x,y,z) in which the rotation axis is defined by the unit vector (0,0,1). The gemstone may be positioned to lie between the source and detector, on the rotation axis.

Data acquisition for obtaining the surface geometry consists of moving the gemstone in steps through different positions relative to the x-ray beam, so that there is a period of motion followed by a stationary time at each position. The path is typically helical so that the source is rotated and raised slightly between adjacent positions. There may be thousands of positions.

For each position, while the gemstone is stationary, an image is taken, e.g. a radiograph—i.e. cone beam projection of X-rays from source point through sample onto large imaging detector. The exposure time for each radiograph is predefined. Each radiograph is a large (e.g. 9 MP) 2D grayscale image.

To reconstruct a three dimensional voxelated grayscale image (a 3D map) from the set of radiographs, any suitable reconstruction method, such as filtered back projection (FBP) or an iterative reconstruction method, may be used.

The grayscale image may be segmented to identify the surface envelope (i.e. surface geometry) of the gemstone.

For the sub-surface mapping step, the following process may be used with the OCT source and detector being contained in a single head through the use of beam splitters.

The gemstone may be positioned or held using the XCT gantry.

Further, the OCT head motion may include translation in x-axis and z-axis and a rotation axis in the y direction (referred to as angle phi). This allows many scanning options for mapping, one is rotation in the xz plane (i.e. y is the rotation axis) about an arbitrary rotation axis.

By mapping the gemstone, multiple co-ordinates for a specific artefact may be captured due to the multiple views from which the sub-surface mapping is performed. Correction of the three dimensional co-ordinates of the specific artefact may be carried out before the whole three dimensional map of artefacts is generated.

Any suitable relative positioning (e.g. other than helical movement) between the gemstone and the mapping devices may be used when surface mapping or sub-surface mapping the gemstone.

According to one example, for data acquisition, an OCT scanning trajectory is defined that will comprise stepwise motion of source and the OCT scan head. One option is to choose the OCT rotation axis to intersect (or nearly intersect) the XCT rotation axis and scan by varying theta and phi space—i.e. cover the sphere of possible angles. The OCT trajectory can be chosen to use the same timing and set of theta angles as the XCT trajectory to allow simultaneous data acquisition. Also, according to another example, continuous motion may be applied where the OCT scan volume is small enough or the OCT is fast enough. For example, the gemstone may rotate around its z-axis while taking line scans from one side.

According to one example, at each position of the sample, the OCT head performs standard acquisition of a deep but narrow 'pencil' OCT scan volume, either Fourier domain or time domain. The size of each OCT scan volume is chosen to overlap with its neighbours. According to another example, a smaller number of wider scans could be used.

Data from each viewing angle is reconstructed using standard OCT techniques, thus creating three dimensional volumes.

Data from multiple viewing angles may be combined on a ray by ray basis using the surface geometry process.

Figure 1B:
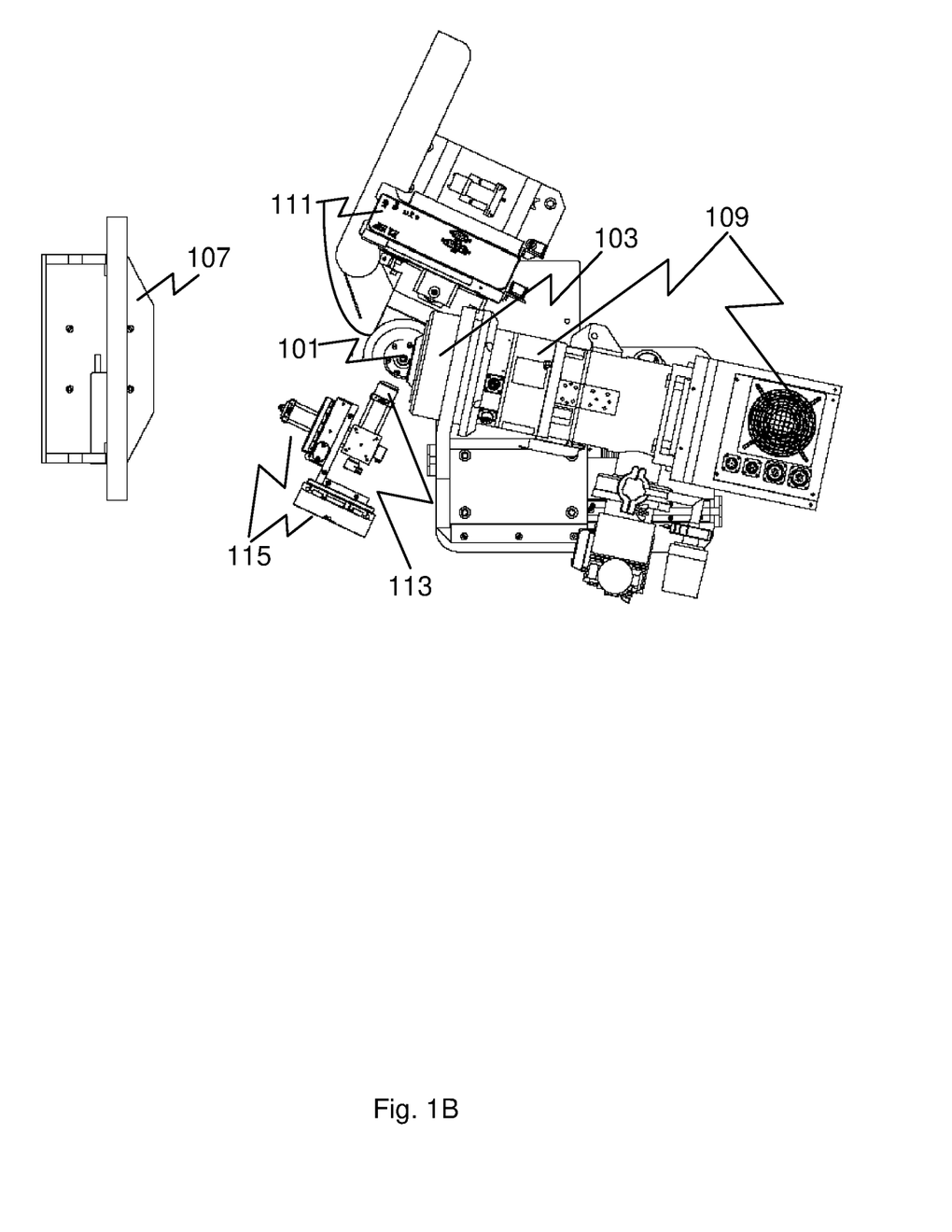
FIG. 1B shows a plan view of the schematic diagram of the system in FIG. 1A.

FIG. 1B shows a plan view of the schematic diagram of FIG. 1A.

FIG. 1B shows a plan view of the system shown in FIG. 1A. The X-ray source 109 emits an X-ray from the X-ray source point 103 towards a detector 107. In this example, the stage 101 rotation and z-axis control 111 are part of the XCT system, although it will be understood that they may also be separate systems. The OCT head (source and detector) 113 movement is controlled by the motion stages 115.

The optical beam may be generated by an optical source as part of any suitable optical tomography process. For example, the sub-surface mapping step may utilise one or more of optical coherence tomography and optical projection tomography processes and and/or machines.

Figure 2A:
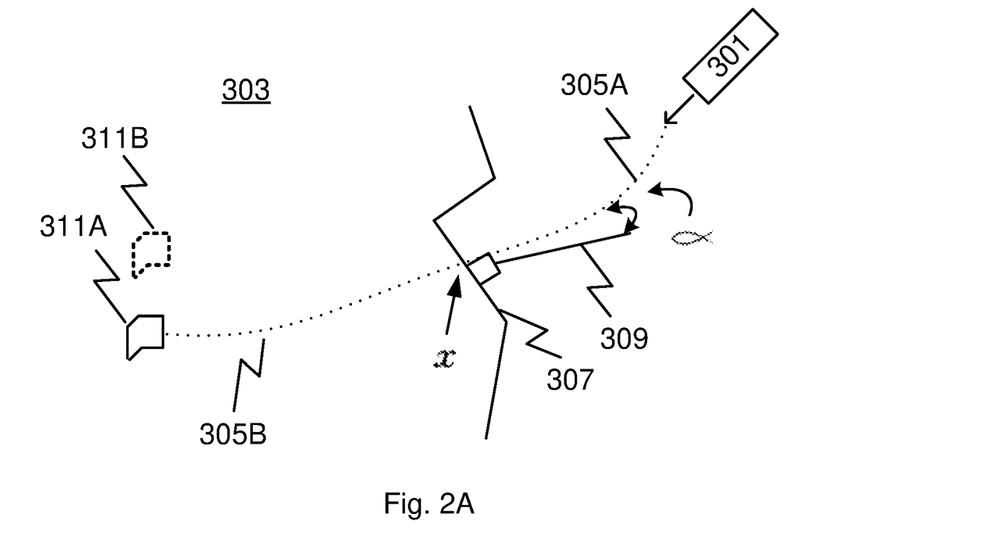
FIGS. 2A and 2B show representations of a beam path impacting a gemstone according to the present disclosure.

FIG. 2A shows one pictorial example of how the three dimensional co-ordinates of visual artefacts may be created. A representation of an optical beam source 301 emitting an optical beam towards a gemstone 303 is shown, where the optical beam path 305A is shown to impact the gemstone at a point x on the surface geometry 307 of the gemstone. It can be seen that the optical beam path is adjusted by the refractive properties of the different mediums (e.g. air and gemstone) in which the beam path is travelling. Further, the optical beam is also diverted based on the angle of incidence at which the beam impacts the surface geometry, where the greater the angle from the surface normal 309, the greater the adjustment or refraction of the optical beam. In this example, the difference (relative positioning) between the optical beam path and the surface normal is indicated as a.

By measuring the back scattering using optical tomography, without any correction for refraction, the OCT mapping equipment measures the back scattering of the optical beam along the optical beam path 305B within the gemstone and determines a location of a visual artefact 311A. A complete sub-surface mapping is carried out across all surface points N, where x=1→N on the surface of the gemstone. Once the mapping is complete, initial three dimensional co-ordinates showing the perceived locations of the visual artefacts, without any correction for refraction, are generated. That is, for example, the perceived locations are of each point where the sub-surface mapping has made a measurement (for the case of OCT the measurement is a reflectance intensity; high levels of reflectance may signify the presence of a visual artefact). These co-ordinates may be used to generate an initial three dimensional map.

Using the relative position at each point x, the initial co-ordinates can be modified by the computing device to adjust for the refraction. The modification therefore identifies the accurate location of the visual artefact 311B and the computing device updates or modifies the initial co-ordinates to generate updated co-ordinates, which may then be used to create an updated map.

Therefore, in general, initial three dimensional co-ordinates of visual artefacts in the gemstone are generated based on an initial sub-surface mapping of the gemstone, and the initial three dimensional co-ordinates are modified based on the determined relative positioning to create modified three dimensional co-ordinates of the visual artefacts.

The initial co-ordinates may be modified by determining an angle of incidence between the optical beam bath and the surface normal. The initial position of the visual artefact using the initial three dimensional co-ordinates is modified based on the angle of incidence and one or more refractive parameters associated with the optical beam path and the gemstone. For example, the refractive parameters may be the refractive index of the one or more media in which the optical beam path travels.

Figure 2B:
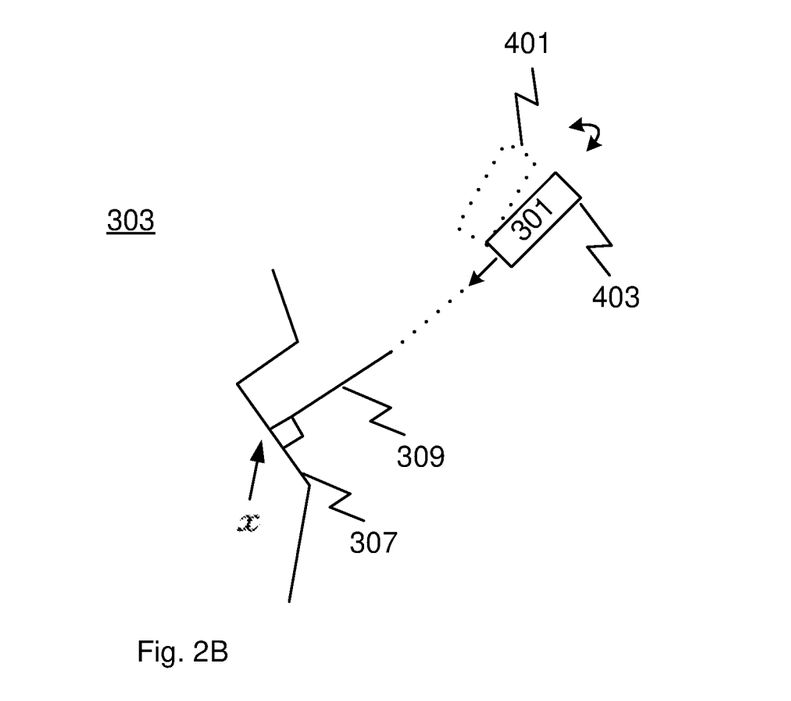

FIG. 2B shows another pictorial example of how the three dimensional co-ordinates of visual artefacts may be generated. The optical beam of the optical source 301 is positioned in an initial position 401 relative to the gemstone. Using the determined angle of incidence (a), the relative position between the optical beam and the gemstone is adjusted so that the optical source can direct the optical beam towards the surface geometry of the gemstone so that the optical beam is perpendicular to the surface of the gemstone. That is, the optical source may be moved to a scanning position 403, or the optical beam may be redirected or adjusted. It will be understood that the gemstone may also be moved, or both the gemstone and optical beam may be moved or adjusted. Also, it will be understood that the optical beam may be adjusted without moving the optical source.

For example, where the gemstone is located on a platform, once the relative positioning between the surface normal and optical beam path is determined for a point x on the surface of the gemstone, during the sub-surface mapping of the gemstone, the platform and the optical source may be moved relative to each other to cause the optical beam path to be substantially in line with the surface normal where the optical beam path intersects with the surface. For rough surfaces, the alignment may not be exact and so the optical beam path may substantially align, or substantially be in line, with the surface normal at the intersection point to at least improve the alignment of the optical beam relative to the surface at the point of intersection so they are at least close (or closer than before) to being ninety degrees to each other. For example, 89 degrees or 88 degrees (or less) may suffice depending on the requirements of the user. For example, the alignment may be based on average alignment values over a defined surface area, where the alignment is therefore an approximation. The system therefore achieves better overall alignment between the optical beam path and the surface normal in the neighbourhood of the intersection point. As a further example, the surface normal may be averaged over the size of the optical beam where the surface normal is found to be not sufficiently flat over the surface area being mapped.

Further, the system may adjust the three dimensional co-ordinates by scaling the distance the artefact is from the surface of the gemstone. The distance the detected artefact is from the surface of the gemstone may be scaled by dividing the distance the artefact is from the surface with the refractive index of the gemstone.

Therefore, according to the two processes depicted in FIGS. 2A and 2B, improved three dimensional co-ordinates of the location of the visual artefacts can be generated in either an adaptive manner, where the relative position of the sub-surface mapping device and gemstone is adjusted during the sub-surface mapping stage to detect and then compute the correct position of the visual artefact in the first instance, or in a non-adaptive manner, where initial co-ordinates are generated identifying the perceived initial location of a visual artefact and the co-ordinates are adjusted or modified to create final co-ordinates that can be used to generate a three dimensional map.

Figure 3A:
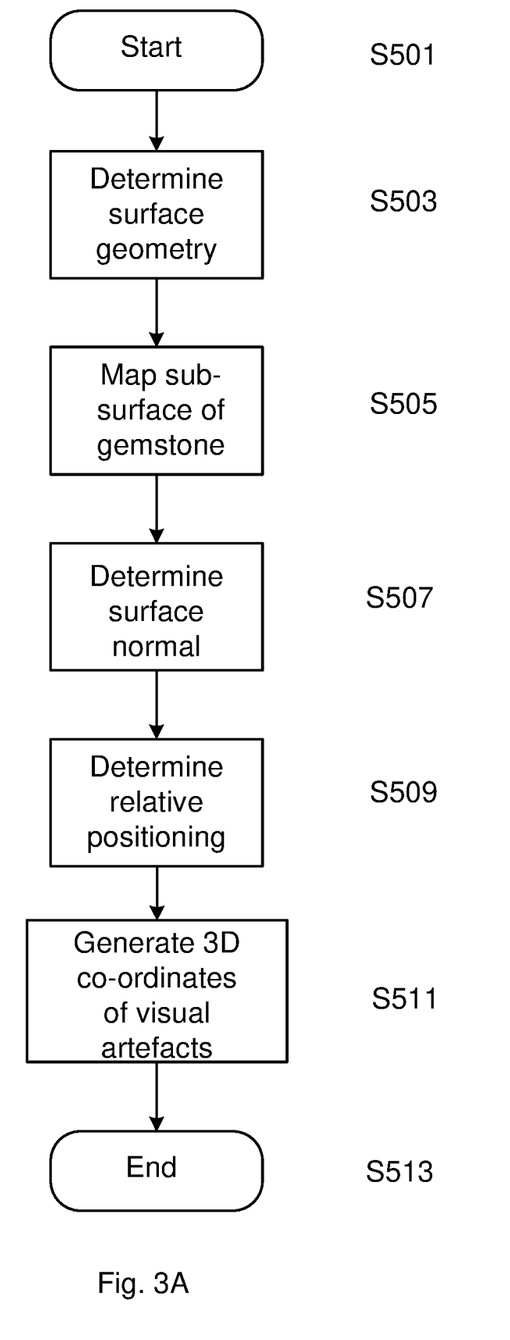
FIGS. 3A to 3C show process flow diagrams according to the present disclosure.

FIG. 3A shows an example process for generating three dimensional co-ordinates. The process starts at step S501. At step S503, the surface geometry of the gemstone is determined. At step S505, the sub-surface of the gemstone is mapped using an optical tomography process. At step S507, the surface normal is determined at the point where the optical beam path intersects the surface geometry. At step S509, the relative positioning between the surface normal and the optical beam path is determined. At step S511, three dimensional co-ordinates of one or more visual artefacts in the gemstone are generated based on the mapping step S505 and the relative positioning determined in step S509. The process ends at step S513.

Figure 3B:
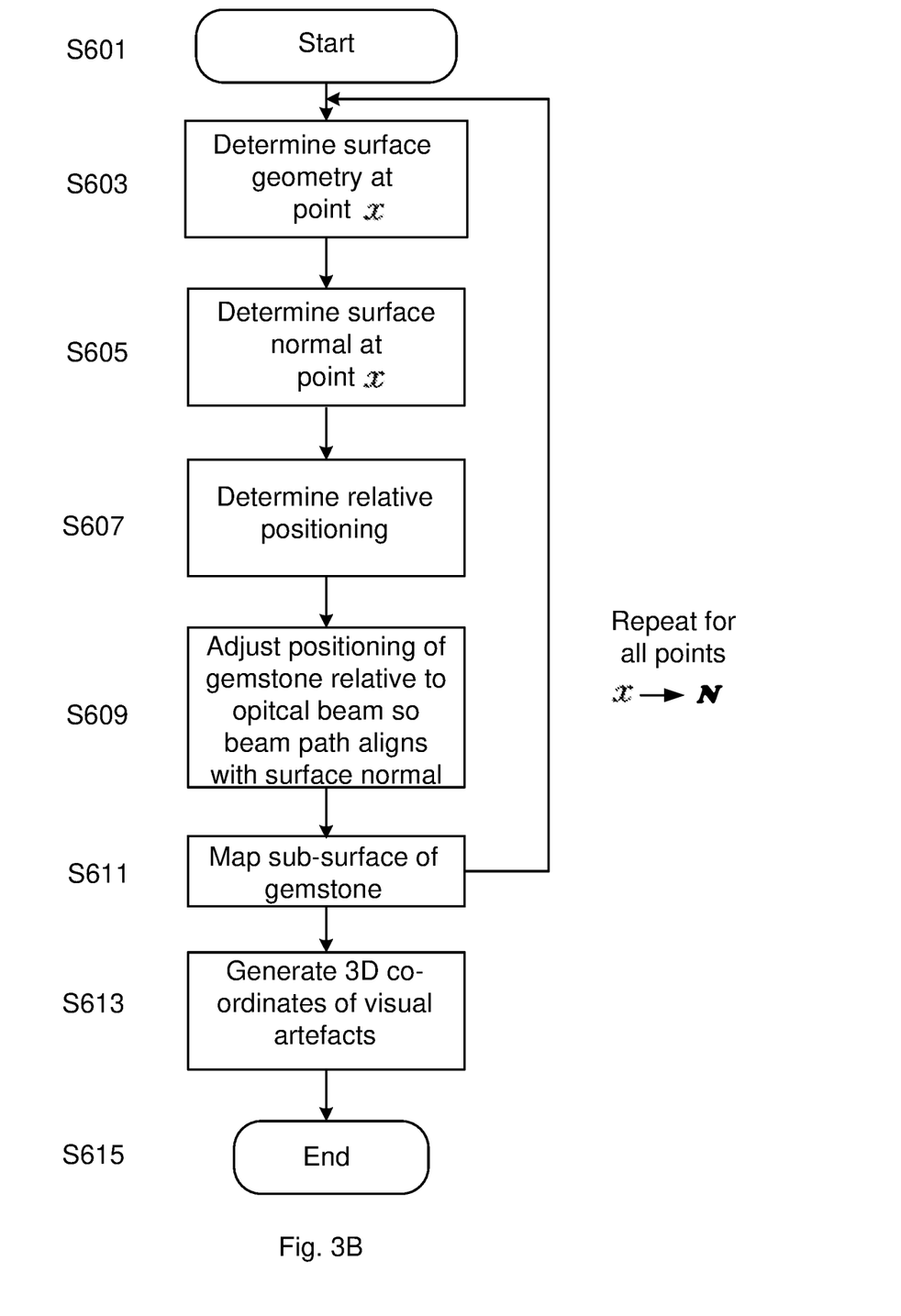

FIG. 3B shows an example process for generating three dimensional co-ordinates. The process starts at step S601. At step S603, the surface geometry of the gemstone at a point x is determined. At step S605, the surface normal is determined at point x. At step S607, the relative positioning between the surface normal and the optical beam path at point x is determined. At step S609, the positioning of the gemstone relative to the optical beam is adjusted so the beam path aligns (or is substantially in-line) with the surface normal where the optical beam path intersects with the surface. At step S611, the sub-surface of the gemstone is mapped at points on the ray path passing through point x using the optical tomography process. Steps S603 to S611 are repeated for all points on the surface of the gemstone. At step S613, three-dimensional co-ordinates of one or more visual artefacts in the gemstone are generated based on the above steps. The process ends at step S615.

Figure 3C:
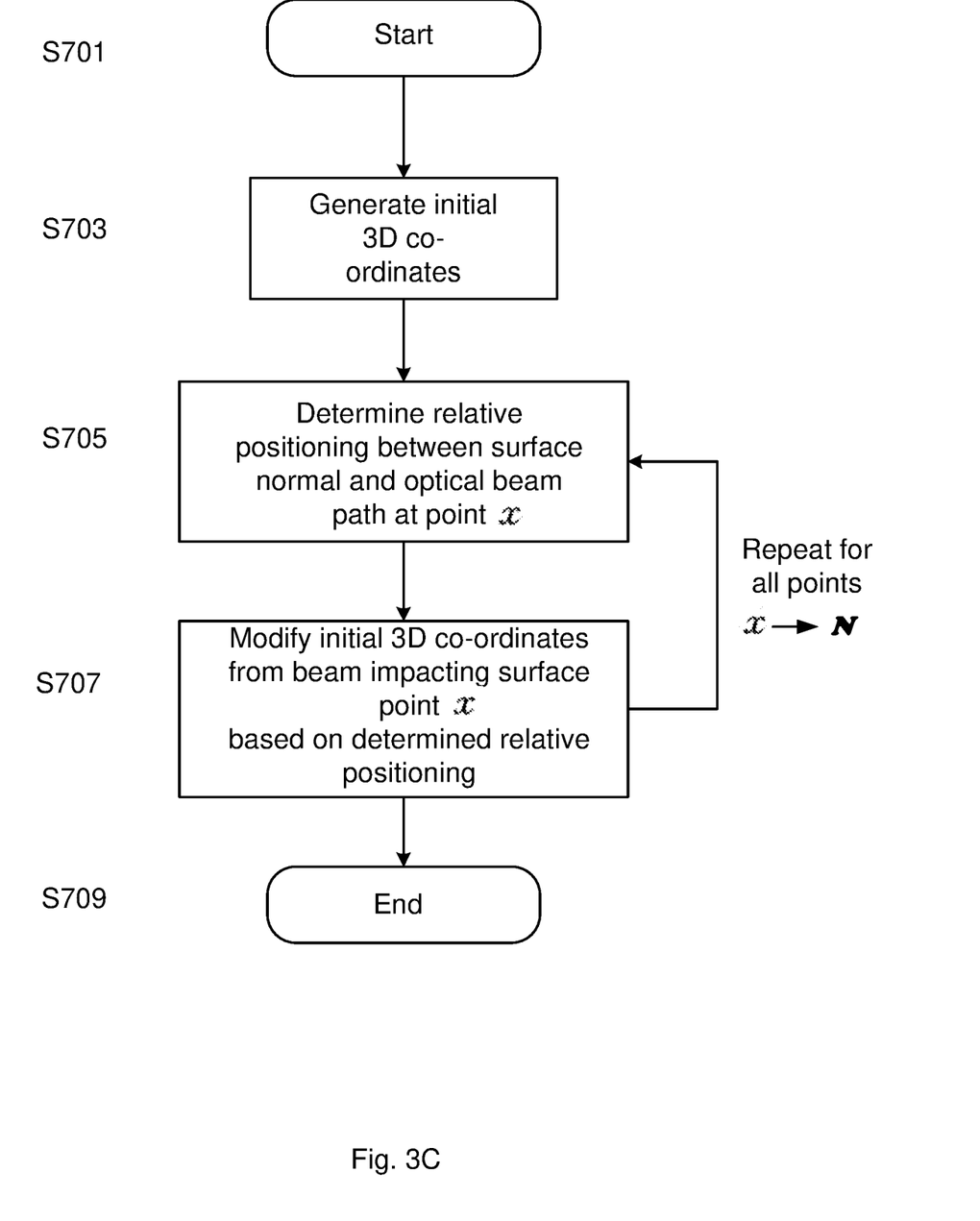

FIG. 3C shows an example process for generating modified three dimensional co-ordinates. The process starts at step S701. At step S703, initial three dimensional co-ordinates are generated. At step S705, the relative positioning between the surface normal and the optical beam path at point x is determined. At step S707, the initial three dimensional co-ordinates are modified, for locations of visual artefacts using a beam impacting the surface at point x, based on the determined relative positioning. Steps S705 and S707 are repeated for all points on the surface of the gemstone. The process ends at step S709.

After performing the aforementioned correction of the three dimensional co-ordinates, a map can be produced if that is desired. An example of how such a map can be generated is now provided.

Step 1: Associated with the corrected sub-surface scan coordinates is a reflectance value that depends on the presence of a visual artefact at that location. To compute the map that is to be produced we store two values per co-ordinate position (x,y,z)::the sum and the count, both these values are initialised to zero.

Step 2: for each point P on each ray from the sub-surface scan, perform steps 3-6.

Step 3: Use P's co-ordinates to determine P's location in the 3D map and label as (x,y,z).

Step 4: Find the 8 nearest grid points in the 3D map to (x,y,z)—if (x,y,z) is in the same coordinates then these 8 points are the 8 combinations of ((int(x), int(y), int(z)) and (int(x)+1, int(y)+1, int(z)+1). That is, the 8 grid points form the corners of the cube inside which the point (x,y,z) lies.

Step 5: Assign weights to each of these points based on their distance to (x,y,z)-closer points have higher weights, and the sum of weights is 1.0.

Step 6: For each of the 8 grid points increment the count value at that position by weight and the sum value at that position by weight*value, where value is the OCT reflectance value at P. This step effectively takes the weighted averages around each point to smooth the result.

Step 7: (after iteration): for all grid points X in the 3D map set map(X) to (0 if Count(X)==0 else Sum(X)/Count(X)).

This produces a map based on scattering intensity values (where OCT is used) or other values associated with the optical tomography process that is used. The detection of a visual artefact is therefore based on the scattering signal (e.g. intensity) measured at a particular point in space (inside the gemstone) by the optical tomography process.

In one example, the surface mapping step for determining surface geometry and the sub-surface mapping step for detecting one or more visual artefacts may be performed simultaneously as a single mapping step. That is, if an optical tomography process, such as OCT, is used to both surface and sub-surface map, the data obtained during the process can be used for both the surface mapping and sub-surface mapping steps. For the simultaneous mapping/sub-surface mapping during the determining of the surface geometry, a local surface geometry associated with a portion of the surface of the gemstone may be determined.

In one example, the surface mapping step may be performed before the sub-surface mapping step. A full mapping of the gemstone surface geometry may be carried out before a full sub-surface mapping of the gemstone begins. Alternatively, a partial surface mapping of the gemstone may be carried out before a partial sub-surface mapping of the gemstone is completed, and the partial surface mapping and sub-surface mapping may be repeated until the whole gemstone is surface and sub-surface mapped.

In one example, XCT data collected before, during and/or subsequent to the surface mapping step may include sub-surface mapping data that can be used to enhance the three dimensional co-ordinates of the visual artefacts that are used to generate the three dimensional map. That is, the system or method describe herein may be arranged to perform the surface mapping step before or after the sub-surface mapping step.

In one example, additional visual artefact information from data collected in an additional sub-surface mapping step may be used to supplement the determination of the three dimensional co-ordinates.

During the surface mapping step, the surface geometry may be determined using one or more of X-ray computed tomography, and optical coherence tomography.

A common platform may be used for both the surface mapping and the sub-surface mapping steps.

Techniques or processes other than X-ray computed tomography and OCT may be used to perform the surface mapping step such as, for example, laser scanning techniques and structured illumination techniques.

The angle of incidence between the optical beam path and the surface normal may be calculated using any suitable means. For example, the surface normal may be calculated using plane fitting to boundary points in the neighbourhood of point x where the optical beam path intersects with the surface of the gemstone. As a further example, where a plane of best fit (D) is determined as Ax+By+Cz=D, the normal is the vector (A,B,C). Alternatively, a direct mesh-based method may be used. Other alternatives are also envisaged.

Snell's law of refraction may be used to compute the refraction of the optical beam path as it enters the gemstone as well as computing the location of each point along the beam path after the optical beam has entered the gemstone.

The three dimensional map identifying the one or more visual artefacts may be generated using the OCT scattering intensity values, for example by interpolating these values in the three dimensional image of the gemstone created during the surface mapping stage.

The point of intersection where the optical beam intersects with the surface of the gemstone may be calculated using any suitable computational geometry e.g. representing the gemstone surface as a triangulated mesh and determining for each triangle in the mesh whether the beam intersects said triangle by computing the point of intersection of the optical beam with an infinite plane that contains said triangle and then checking if the intersection point lies inside the triangle.

A generated image may be improved by maximising visual artefact detection overlap during the sub-surface mapping stage. That is, multiple views (co-ordinate generation) into each interior location of the gemstone may be used to improve accuracy of the location determination of the artefact, for example. Therefore, the determined location of visual artefacts (for example) may be refined and adjusted based on the consistency of sub-surface mapping results obtained from different viewing angles or at different surface intersection points. This consistency mapping process may also use XCT data or data from other sources in order to improve the accuracy of the location determination of the artefact, for example.

Figure 4A:
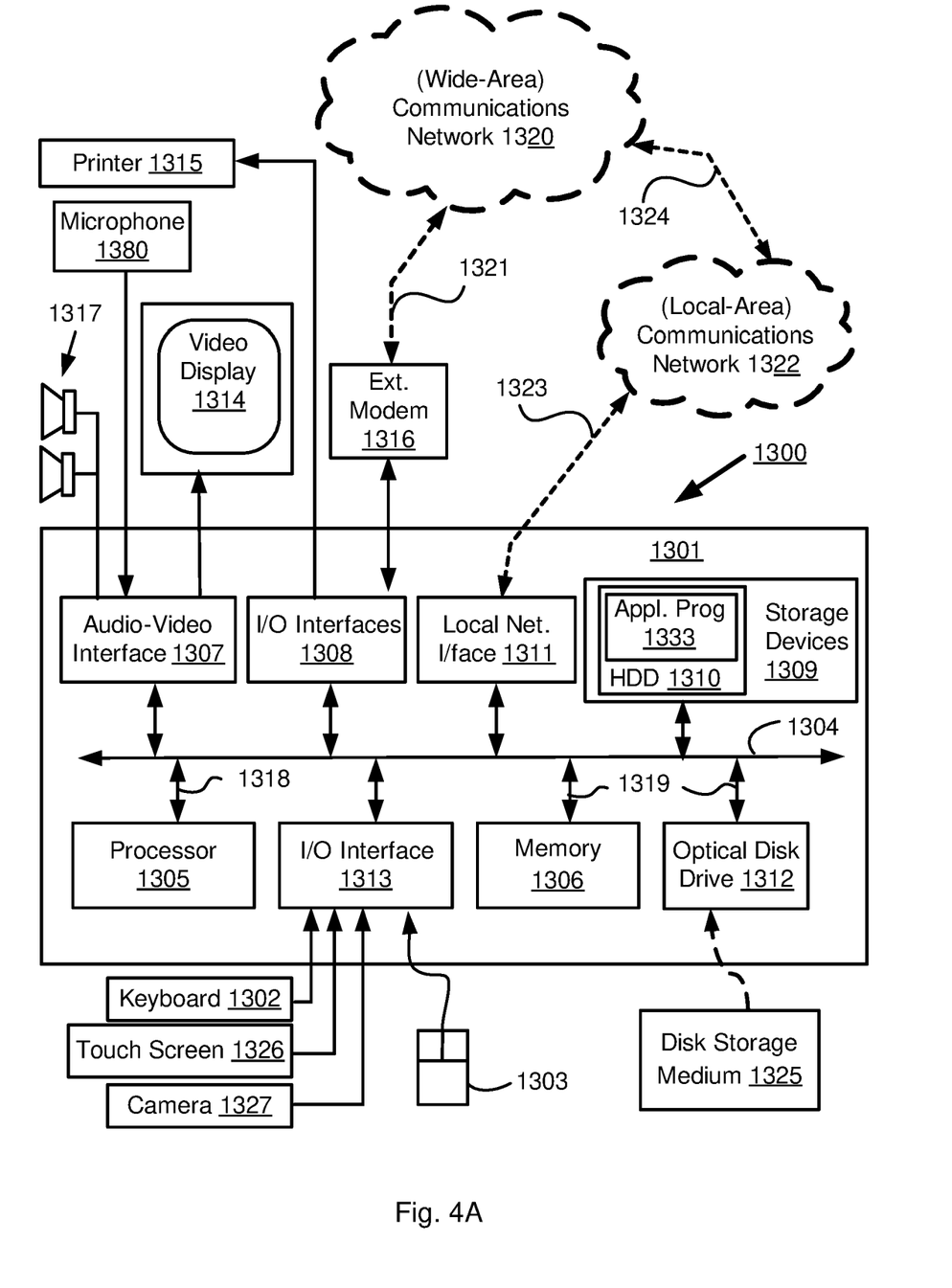
FIGS. 4A and 4B form a schematic block diagram of a computer system forming part of the system arranged to determine the location of artefacts, and is arranged to carry out the processes described in relation to FIGS. 3A to 3C and other processes described herein.
Figure 4B:
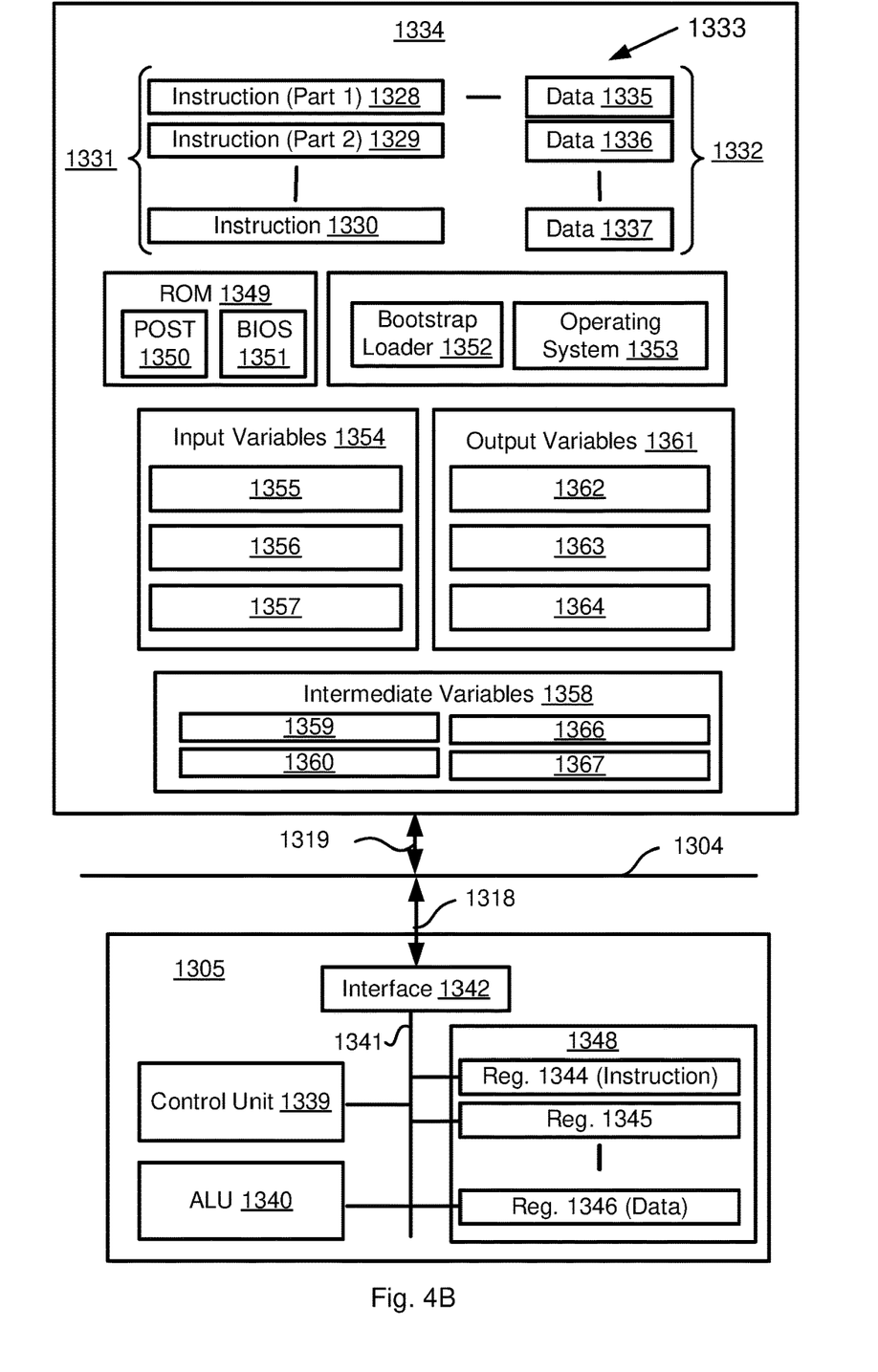

FIGS. 4A and 4B depict a general-purpose computer system 1300, upon which the various arrangements described can be practiced and/or the methods described can be implemented and controlled.

As seen in FIG. 4A, the computer system 1300 includes: a computer module 1301; input devices such as a keyboard 1302, a mouse pointer device 1303, a touch screen 1326, a camera 1327, and a microphone 1380; and output devices including a printer 1315, a display device 1314 and loudspeakers 1317. An external Modulator-Demodulator (Modem) transceiver device 1316 may be used by the computer module 1301 for communicating to and from a communications network 1320 via a connection 1321. The communications network 1320 may be a wide-area network (WAN), such as the Internet, a cellular telecommunications network, or a private WAN. Where the connection 1321 is a telephone line, the modem 1316 may be a traditional "dial-up" modem. Alternatively, where the connection 1321 is a high capacity (e.g., cable) connection, the modem 1316 may be a broadband modem. A wireless modem may also be used for wireless connection to the communications network 1320.

The computer module 1301 typically includes at least one processor unit 1305, and a memory unit 1306. For example, the memory unit 1306 may have semiconductor random access memory (RAM) and semiconductor read only memory (ROM). The computer module 1301 also includes an number of input/output (I/O) interfaces including: an audio-video interface 1307 that couples to the video display 1314, loudspeakers 1317 and microphone 1380; an I/O interface 1313 that couples to the keyboard 1302, mouse 1303, scanner 1326, camera 1327 and optionally a joystick or other human interface device (not illustrated); and an interface 1308 for the external modem 1316 and printer 1315. In some implementations, the modem 1316 may be incorporated within the computer module 1301, for example within the interface 1308. The computer module 1301 also has a local network interface 1311, which permits coupling of the computer system 1300 via a connection 1323 to a local-area communications network 1322, known as a Local Area Network (LAN). As illustrated in FIG. 4A, the local communications network 1322 may also couple to the wide network 1320 via a connection 1324, which would typically include a so-called "firewall" device or device of similar functionality. The local network interface 1311 may comprise an Ethernet circuit card, a Bluetooth® wireless arrangement or an IEEE 802.11 wireless arrangement; however, numerous other types of interfaces may be practiced for the interface 1311.

The I/O interfaces 1308 and 1313 may afford either or both of serial and parallel connectivity, the former typically being implemented according to the Universal Serial Bus (USB) standards and having corresponding USB connectors (not illustrated). Storage devices 1309 are provided and typically include a hard disk drive (HDD) 1310. Other storage devices such as a floppy disk drive and a magnetic tape drive (not illustrated) may also be used. An optical disk drive 1312 is typically provided to act as a non-volatile source of data. Portable memory devices, such optical disks (e.g., CD-ROM, DVD, Blu-ray Disc™), USB-RAM, portable, external hard drives, and floppy disks, for example, may be used as appropriate sources of data to the system 1300.

The components 1305 to 1313 of the computer module 1301 typically communicate via an interconnected bus 1304 and in a manner that results in a conventional mode of operation of the computer system 1300 known to those in the relevant art. For example, the processor 1305 is coupled to the system bus 1304 using a connection 1318. Likewise, the memory 1306 and optical disk drive 1312 are coupled to the system bus 1304 by connections 1319. Examples of computers on which the described arrangements can be practised include IBM-PC's and compatibles, Apple Mac™ or like computer systems.

The method of detecting visual artefacts may be implemented using the computer system 1300 wherein the processes of FIGS. 3A-3C described herein, may be implemented as one or more software application programs 1333 executable within the computer system 1300. In particular, the steps of the method of detecting visual artefacts are effected by instructions 1331 (see FIG. 4B) in the software 1333 that are carried out within the computer system 1300. The software instructions 1331 may be formed as one or more code modules, each for performing one or more particular tasks. The software may also be divided into two separate parts, in which a first part and the corresponding code modules performs the visual artefact detection methods and a second part and the corresponding code modules manage a user interface between the first part and the user.

The software may be stored in a computer readable medium, including the storage devices described below, for example. The software is loaded into the computer system 1300 from the computer readable medium, and then executed by the computer system 1300. A computer readable medium having such software or computer program recorded on the computer readable medium is a computer program product. The use of the computer program product in the computer system 1300 preferably effects an advantageous apparatus for detecting visual artefacts.

The software 1333 is typically stored in the HDD 1310 or the memory 1306. The software is loaded into the computer system 1300 from a computer readable medium, and executed by the computer system 1300. Thus, for example, the software 1333 may be stored on an optically readable disk storage medium (e.g., CD-ROM) 1325 that is read by the optical disk drive 1312. A computer readable medium having such software or computer program recorded on it is a computer program product. The use of the computer program product in the computer system 1300 preferably effects an apparatus for detecting visual artefacts.

In some instances, the application programs 1333 may be supplied to the user encoded on one or more CD-ROMs 1325 and read via the corresponding drive 1312, or alternatively may be read by the user from the networks 1320 or 1322. Still further, the software can also be loaded into the computer system 1300 from other computer readable media. Computer readable storage media refers to any non-transitory tangible storage medium that provides recorded instructions and/or data to the computer system 1300 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a PCMCIA card and the like, whether or not such devices are internal or external of the computer module 1301. Examples of transitory or non-tangible computer readable transmission media that may also participate in the provision of software, application programs, instructions and/or data to the computer module 1301 include radio or infra-red transmission channels as well as a network connection to another computer or networked device, and the Internet or Intranets including e-mail transmissions and information recorded on Websites and the like.

The second part of the application programs 1333 and the corresponding code modules mentioned above may be executed to implement one or more graphical user interfaces (GUIs) to be rendered or otherwise represented upon the display 1314. Through manipulation of typically the keyboard 1302 and the mouse 1303, a user of the computer system 1300 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 1317 and user voice commands input via the microphone 1380.

FIG. 4B is a detailed schematic block diagram of the processor 1305 and a "memory" 1334. The memory 1334 represents a logical aggregation of all the memory modules (including the HDD 1309 and semiconductor memory 1306) that can be accessed by the computer module 1301 in FIG. 4A.

When the computer module 1301 is initially powered up, a power-on self-test (POST) program 1350 executes. The POST program 1350 is typically stored in a ROM 1349 of the semiconductor memory 1306 of FIG. 4A. A hardware device such as the ROM 1349 storing software is sometimes referred to as firmware. The POST program 1350 examines hardware within the computer module 1301 to ensure proper functioning and typically checks the processor 1305, the memory 1334 (1309, 1306), and a basic input-output systems software (BIOS) module 1351, also typically stored in the ROM 1349, for correct operation. Once the POST program 1350 has run successfully, the BIOS 1351 activates the hard disk drive 1310 of FIG. 4A. Activation of the hard disk drive 1310 causes a bootstrap loader program 1352 that is resident on the hard disk drive 1310 to execute via the processor 1305. This loads an operating system 1353 into the RAM memory 1306, upon which the operating system 1353 commences operation. The operating system 1353 is a system level application, executable by the processor 1305, to fulfil various high level functions, including processor management, memory management, device management, storage management, software application interface, and generic user interface.

The operating system 1353 manages the memory 1334 (1309, 1306) to ensure that each process or application running on the computer module 1301 has sufficient memory in which to execute without colliding with memory allocated to another process. Furthermore, the different types of memory available in the system 1300 of FIG. 4A must be used properly so that each process can run effectively. Accordingly, the aggregated memory 1334 is not intended to illustrate how particular segments of memory are allocated (unless otherwise stated), but rather to provide a general view of the memory accessible by the computer system 1300 and how such is used.

As shown in FIG. 4B, the processor 1305 includes a number of functional modules including a control unit 1339, an arithmetic logic unit (ALU) 1340, and a local or internal memory 1348, sometimes called a cache memory. The cache memory 1348 typically includes a number of storage registers 1344-1346 in a register section. One or more internal busses 1341 functionally interconnect these functional modules. The processor 1305 typically also has one or more interfaces 1342 for communicating with external devices via the system bus 1304, using a connection 1318. The memory 1334 is coupled to the bus 1304 using a connection 1319.

The application program 1333 includes a sequence of instructions 1331 that may include conditional branch and loop instructions. The program 1333 may also include data 1332 which is used in execution of the program 1333. The instructions 1331 and the data 1332 are stored in memory locations 1328, 1329, 1330 and 1335, 1336, 1337, respectively. Depending upon the relative size of the instructions 1331 and the memory locations 1328-1330, a particular instruction may be stored in a single memory location as depicted by the instruction shown in the memory location 1330. Alternately, an instruction may be segmented into a number of parts each of which is stored in a separate memory location, as depicted by the instruction segments shown in the memory locations 1328 and 1329.

In general, the processor 1305 is given a set of instructions which are executed therein. The processor 1305 waits for a subsequent input, to which the processor 1305 reacts to by executing another set of instructions. Each input may be provided from one or more of a number of sources, including data generated by one or more of the input devices 1302, 1303, data received from an external source across one of the networks 1320, 1302, data retrieved from one of the storage devices 1306, 1309 or data retrieved from a storage medium 1325 inserted into the corresponding reader 1312, all depicted in FIG. 4A. The execution of a set of the instructions may in some cases result in output of data. Execution may also involve storing data or variables to the memory 1334.

The disclosed visual artefact detecting arrangements use input variables 1354, which are stored in the memory 1334 in corresponding memory locations 1355, 1356, 1357. The visual artefact detecting arrangements produce output variables 1361, which are stored in the memory 1334 in corresponding memory locations 1362, 1363, 1364. Intermediate variables 1358 may be stored in memory locations 1359, 1360, 1366 and 1367.

Referring to the processor 1305 of FIG. 4B, the registers 1344, 1345, 1346, the arithmetic logic unit (ALU) 1340, and the control unit 1339 work together to perform sequences of micro-operations needed to perform "fetch, decode, and execute" cycles for every instruction in the instruction set making up the program 1333. Each fetch, decode, and execute cycle comprises:

a fetch operation, which fetches or reads an instruction 1331 from a memory location 1328, 1329, 1330;

a decode operation in which the control unit 1339 determines which instruction has been fetched; and an execute operation in which the control unit 1339 and/or the ALU 1340 execute the instruction.

Thereafter, a further fetch, decode, and execute cycle for the next instruction may be executed. Similarly, a store cycle may be performed by which the control unit 1339 stores or writes a value to a memory location 1332.

Each step or sub-process in the processes of FIGS. 3A-3C is associated with one or more segments of the program 1333 and is performed by the register section 1344, 1345, 1347, the ALU 1340, and the control unit 1339 in the processor 1305 working together to perform the fetch, decode, and execute cycles for every instruction in the instruction set for the noted segments of the program 1333.

The method of detecting visual artefacts may alternatively be implemented in dedicated hardware such as one or more integrated circuits performing the functions or sub functions of detecting visual artefacts. Such dedicated hardware may include graphic processors, digital signal processors, or one or more microprocessors and associated memories.

INDUSTRIAL APPLICABILITY

The arrangements described are applicable to industries processing gemstones, minerals or samples thereof, and optical data processing industries in general.

The foregoing describes only some embodiments of the present invention, and modifications and/or changes can be made thereto without departing from the scope and spirit of the invention, the embodiments being illustrative and not restrictive.

In the context of this specification, the word "comprising" means "including principally but not necessarily solely" or "having" or "including", and not "consisting only of". Variations of the word "comprising", such as "comprise" and "comprises" have correspondingly varied meanings.

The invention claimed is:

1. A method for determining a location of artefacts and/or inclusions in a gemstone, mineral or sample thereof, the method comprising the steps of:

surface mapping a gemstone, mineral or sample thereof to determine surface geometry associated with at least a portion of a surface of the gemstone, mineral or sample thereof;

sub-surface mapping the gemstone, mineral or sample thereof using an optical beam that is directed at the surface along an optical beam path, wherein the optical beam is generated by an optical source using an optical tomography process;

determining a surface normal at the surface at an intersection point between the optical beam path and the determined surface geometry;

determining relative positioning between the surface normal and the optical beam path;

determining the location of artefacts and/or inclusions in the gemstone, mineral or sample thereof based on the sub-surface mapping step and the determined relative positioning; and wherein, based on the determined relative positioning, during the sub-surface mapping of the gemstone, mineral or sample thereof, the gemstone, mineral or sample thereof, and the optical beam are moved relative to each other to cause the optical beam path to be substantially in line with the surface normal where the optical beam path intersects with the surface.

2. The method of claim 1, wherein the step of determining the location of the artefacts and/or inclusions comprises the steps of generating an initial set of three dimensional co-ordinates of the artefacts and/or inclusions in the gemstone, mineral or sample thereof based on an initial sub-surface mapping of the gemstone, mineral or sample thereof; and modifying the initial three dimensional co-ordinates based on the determined relative positioning to create modified three dimensional co-ordinates of the artefacts and/or inclusions.

3. The method of claim 2, wherein the modifying step comprises determining an angle of incidence between the optical beam path and the surface normal, and modifying the initial three dimensional co-ordinates based on the angle of incidence and one or more refractive parameters associated with the optical beam path and the gemstone, mineral or sample thereof.

4. The method of claim 1, wherein the surface mapping step and sub-surface mapping step are performed simultaneously as a single mapping step.

5. The method of claim 1, wherein the surface mapping step is performed before or after the sub-surface mapping step.

6. The method of claim 1, wherein the surface mapping step comprises determining the surface geometry using one or more of X-ray computed tomography, optical coherence tomography, laser scanning, and structured illumination.

7. The method of claim 1, wherein the sub-surface mapping step comprises using one or more of optical coherence tomography and optical projection tomography.

8. The method of claim 1, comprising the step of refining a determined location of the artefacts and/or inclusions based on consistency between sub-surface mapping results obtained from different viewing angles or at different surface intersection points on the surface of the gemstone, mineral or sample thereof.

9. The method of claim 1, where the step of determining the location comprises the steps of determining three dimensional co-ordinates of the location of the artefacts and/or inclusions, and generating a three dimensional map based on the determined three dimensional co-ordinates.

10. A system for determining a location of artefacts and/or inclusions in a gemstone, mineral or sample thereof, the system comprising:
   a surface mapping device arranged to surface map a gemstone, mineral or sample thereof to determine surface geometry associated with at least a portion of a surface of the gemstone, mineral or sample thereof;
   a sub-surface mapping device arranged to sub-surface map the gemstone, mineral or sample thereof using an optical beam that is directed at the surface along an optical beam path, wherein the optical beam is generated by an optical source using an optical tomography process; and
   a computing system arranged to:
      determine a surface normal at the surface at an intersection point between the optical beam path and the determined surface geometry,
      determine relative positioning between the surface normal and the optical beam path, and
      determine the location of artefacts and/or inclusions in the gemstone, mineral or sample thereof based on the sub-surface mapping step and the determined relative positioning,
   wherein, based on the determined relative positioning, during the sub-surface mapping of the gemstone, mineral or sample thereof, the gemstone, mineral or sample thereof, and the optical beam are moved relative to each other to cause the optical beam path to be substantially in line with the surface normal where the optical beam path intersects with the surface.

11. The system of claim 10, wherein the system is arranged to determine the location of the artefacts and/or inclusions by generating an initial set of three dimensional co-ordinates of the artefacts and/or inclusions in the gemstone, mineral or sample thereof based on an initial sub-surface mapping of the gemstone, mineral or sample thereof; and modifying the initial three dimensional co-ordinates based on the determined relative positioning to create modified three dimensional co-ordinates of the artefacts and/or inclusions.

12. The system of claim 11, wherein the system is arranged to modify the initial three dimensional co-ordinates by determining an angle of incidence between the optical beam bath and the surface normal, and modifying the initial three dimensional co-ordinates based on the angle of incidence and one or more refractive parameters associated with the optical beam path and the gemstone, mineral or sample thereof.

13. The system of claim 10, wherein the system is arranged to perform the surface mapping step and sub-surface mapping step simultaneously as a single mapping step.

14. The system of claim 10, wherein the system is arranged to perform the surface mapping step before or after the sub-surface mapping step.

15. The system of claim 10, wherein the surface mapping device is arranged to determine the surface geometry using one or more of X-ray computed tomography, optical coherence tomography, laser scanning, and structure illumination.

16. The system of claim 10, wherein the sub-surface mapping device is arranged to map the sub-surface using one or more of optical coherence tomography and optical projection tomography.

17. The system of claim 10, wherein the computing system is arranged to refine a determined location of the artefacts and/or inclusions based on consistency between sub-surface mapping results obtained from different viewing angles or at different surface intersection points on the surface of the gemstone, mineral or sample thereof.

18. The system of claim 10, wherein the computing system is arranged to determine the location of the artefacts and/or inclusions by determining three dimensional co-ordinates of the location of the artefacts and/or inclusions, and generating a three dimensional map based on the determined three dimensional co-ordinates.

* * * * *